United States Patent
Burkman et al.

(10) Patent No.: US 8,390,681 B1
(45) Date of Patent: Mar. 5, 2013

(54) COMPUTER ASSISTED SEMEN ANALYZER TO ANALYZE DIGITAL VIDEO CLIPS RECEIVED FROM A REMOTE LOCATION

(75) Inventors: Lani J. Burkman, Grand Island, NY (US); Fadi Joulak, Williamsville, NY (US)

(73) Assignee: LifeCell Dx, Inc., Buffalo, NY (US)

( * ) Notice: Subject to any disclaimer, the term of this patent is extended or adjusted under 35 U.S.C. 154(b) by 262 days.

(21) Appl. No.: 12/645,238

(22) Filed: Dec. 22, 2009

Related U.S. Application Data (60) Provisional application No. 61/203,348, filed on Dec. 23, 2008.

(51) Int. Cl.
*G06F 15/16* (2006.01)
(52) U.S. Cl. .............. 348/79; 348/80; 709/217; 435/4; 435/34
(58) Field of Classification Search .......... 348/79, 348/80; 434/34, 287.1; 435/4, 34; 709/217
See application file for complete search history.

(56) References Cited

U.S. PATENT DOCUMENTS

| | | | |
|---|---|---|---|
| 5,358,847 | A | 10/1994 | Brown |
| 6,426,213 | B1 | 7/2002 | Eisenson |
| 6,445,451 | B1 | 9/2002 | Douglas-Hamilton et al. |
| 7,070,917 | B1 | 7/2006 | Christensen et al. |
| 7,252,642 | B2 * | 8/2007 | Kislev et al. ................. 600/578 |
| 2002/0165673 | A1 | 11/2002 | Morgan |
| 2003/0148365 | A1 | 8/2003 | Morgan |
| 2004/0021666 | A1 * | 2/2004 | Soll et al. ................. 345/474 |
| 2004/0146848 | A1 * | 7/2004 | Kislev et al. ................. 435/4 |
| 2006/0109343 | A1 * | 5/2006 | Watanabe et al. ............. 348/79 |
| 2006/0251294 | A1 * | 11/2006 | Soll et al. ................. 382/107 |
| 2007/0196811 | A1 * | 8/2007 | Torres Simon et al. ........ 435/1.3 |
| 2007/0238680 | A1 * | 10/2007 | Dehn et al. ................... 514/44 |
| 2007/0245812 | A1 * | 10/2007 | Kislev et al. ................ 73/61.41 |
| 2007/0298454 | A1 * | 12/2007 | Green et al. ................. 435/34 |
| 2009/0238423 | A1 | 9/2009 | Rigler |

FOREIGN PATENT DOCUMENTS

| | | |
|---|---|---|
| WO | WO9941578 A1 | 8/1999 |
| WO | WO9956133 A1 | 11/1999 |
| WO | WO2007038232 A3 | 4/2007 |
| WO | WO2007085839 A1 | 8/2007 |
| WO | WO2008009403 A1 | 1/2008 |

OTHER PUBLICATIONS

IVOS Sperm Analyzer, Hamilton Thorne, Sep. 2008, www.hamiltonthrone.com, pp. 1-7.*

Human Sperm Hyperactivation and CASA analysis as a rapid QC/toxicity assay. Presented at the 50th annual meeting of the American Fertility Society, Nov. 5-10, 1994, San Antonio, program supplement p. S174.

(Continued)

*Primary Examiner* — Haresh N Patel
(74) *Attorney, Agent, or Firm* — Brian B. Shaw, Esq.; Jodi A. Reynolds, Esq.; Harter Secrest & Emery LLP (57) ABSTRACT

A method of analyzing a semen sample having living sperm is provided comprising receiving from a remote location a set of digital video clips of a prepared semen sample having living sperm and analyzing a subset of the digital video clips taken from the prepared semen sample using a Computer Assisted Semen Analyzer adapted to analyze the subset of digital video clips received from a remote location. A method of measuring sperm morphology is also provided comprising receiving from a remote location a digital video clip of a prepared semen sample having stained non-living sperm, and, analyzing portions of the digital video clip taken from the prepared semen sample.

9 Claims, 9 Drawing Sheets

OTHER PUBLICATIONS

Sperm Hyperactivation (HA) as a Critical Part of the Semen Analysis: Predicting Pregnancy versus Long Term Infertility. Am Soc for Reprod Medicine, 1996; S-12 Abstract, Dec. 31 p. S-12.

Provisional U.S. Appl. No. 61/203,348, filed Dec. 23, 2008, p. 1.
Provisional U.S. Appl. No. 60/952,919, filed Jul. 31, 2007, p. 1.

* cited by examiner

COMPUTER ASSISTED SEMEN ANALYZER TO ANALYZE DIGITAL VIDEO CLIPS RECEIVED FROM A REMOTE LOCATION

CROSS-REFERENCE TO RELATED APPLICATIONS

This application claims the benefit of, and incorporates by reference, U.S. Provisional Patent Application No. 61/203,348, filed Dec. 23, 2008.

STATEMENT REGARDING FEDERALLY SPONSORED RESEARCH OR DEVELOPMENT

Not applicable.

REFERENCE TO A "SEQUENCE LISTING"

Not applicable.

BACKGROUND OF THE INVENTION

1. Field of the Invention

The present invention relates to methods of analyzing sperm and devices relating thereto, and more particularly, the present invention relates to analyzing digital video clips of semen samples that are received from a remote location. The present invention also relates to the use of contraceptives in mammals, and more particularly, to the use of a contraceptive for males and females utilizing a cannabinoid ligand.

2. Description of Related Art

There are more than 13 million infertile couples world wide. However, less than 1% of the cities in the U.S., and worldwide, have a laboratory which can carry out a semen analysis by a trained "andrologist." One out of every five couples will require help in achieving a pregnancy and typically must have a semen analysis. The old-fashioned semen analysis (sperm count, % moving) cannot predict whether the man is fertile or not (see references). Today, most infertile couples who desire an advanced semen test may have to travel to distant Andrology labs, perhaps 4 to 10 hours away. This is both costly and stressful, often leading to an inferior sperm sample. A majority of couples simply do not have access to any laboratory that can provide an excellent semen report. Further, since sperm have a short life span (1-2 hours), a patient is under the duress of watching the clock, rushing the sample to the nearest hospital or reference laboratory, or collecting the sample away from home and in stressful surroundings (lab collection room; hotel; etc.).

In addition, the quality of equipment and technician training varies significantly from laboratory to laboratory, and doctors do not have many laboratory options to present to the patients.

What is needed, then, is a method for providing patients with access to a distant sperm diagnostic laboratory that can perform reasonably accurate and sophisticated semen analysis, without requiring a patient to travel long distances.

What is also needed is a method and system for using telemedicine to receive semen sample data from a remote location.

A need also exists for a method of preparing a semen sample for telemedicine analysis that approximates a predetermined profile.

Further, a need exists for a method of measuring sperm morphology from a remote location.

Also, a need exists for a method of sperm morphology evaluation that can ascertain the male's fertilizing potential.

The various methods and embodiments disclosed herein overcome the deficiencies described above with respect to known methods and devices for analyzing a semen sample.

BRIEF SUMMARY OF THE INVENTION

The present invention generally includes a method of analyzing a semen sample having living sperm. The method includes receiving from a remote location a set of digital video clips of a prepared semen sample having living sperm, and analyzing a subset of the digital video clips taken from the prepared semen sample using a Computer Assisted Semen Analyzer adapted to analyze the subset of digital video clips received from a remote location.

The method also includes warming the semen sample to approximately 37 degrees Celsius using a semen chamber warming device and capturing the set of digital video clips of the prepared semen sample with a camera coupled to a microscope. In an embodiment of the invention, the microscope is set to dark field viewing. The digital video clips are captured at a rate of at least 50 images per second. In an embodiment of the invention, the digital video clips are captured at a rate of 60 images per second.

The digital video clips may be transmitted over the internet between two geographically separate facilities located in any part of the world.

The present invention further comprises a method of preparing a semen sample for remote analysis. The method includes the step of receiving a semen sample having living sperm in a predetermined volume of liquid medium, comparing the semen sample to a predetermined profile, determining whether the semen sample approximates the predetermined profile and preparing a dilution of the semen sample corresponding to the determining step. The semen sample is diluted further until the semen sample approximates the predetermined profile. The semen sample is not diluted if the semen sample approximates the predetermined profile without diluting.

Further, the present invention includes a method of measuring sperm morphology including the steps of receiving from a remote location a digital video clip of a prepared semen sample having stained non-living sperm and analyzing portions of the digital video clip taken from the prepared semen sample by means of playback via a computer. In an embodiment of the invention, the digital video clip used for measuring sperm morphology is approximately five to approximately ten seconds in duration and is recorded by moving a slide in a predetermined pattern using a non-continuous motion.

Also, the present invention includes a centrifuge comprising a base, two arms moveable between a resting position and an open position, and, at least one aperture at a distal end of each arm.

The invention will now be described in detail in terms of the drawings and the description which follow.

DETAILED DESCRIPTION OF THE INVENTION

At the outset, it should be appreciated that the use of the same reference number throughout the several figures designates a like or similar element.

Figure 1:
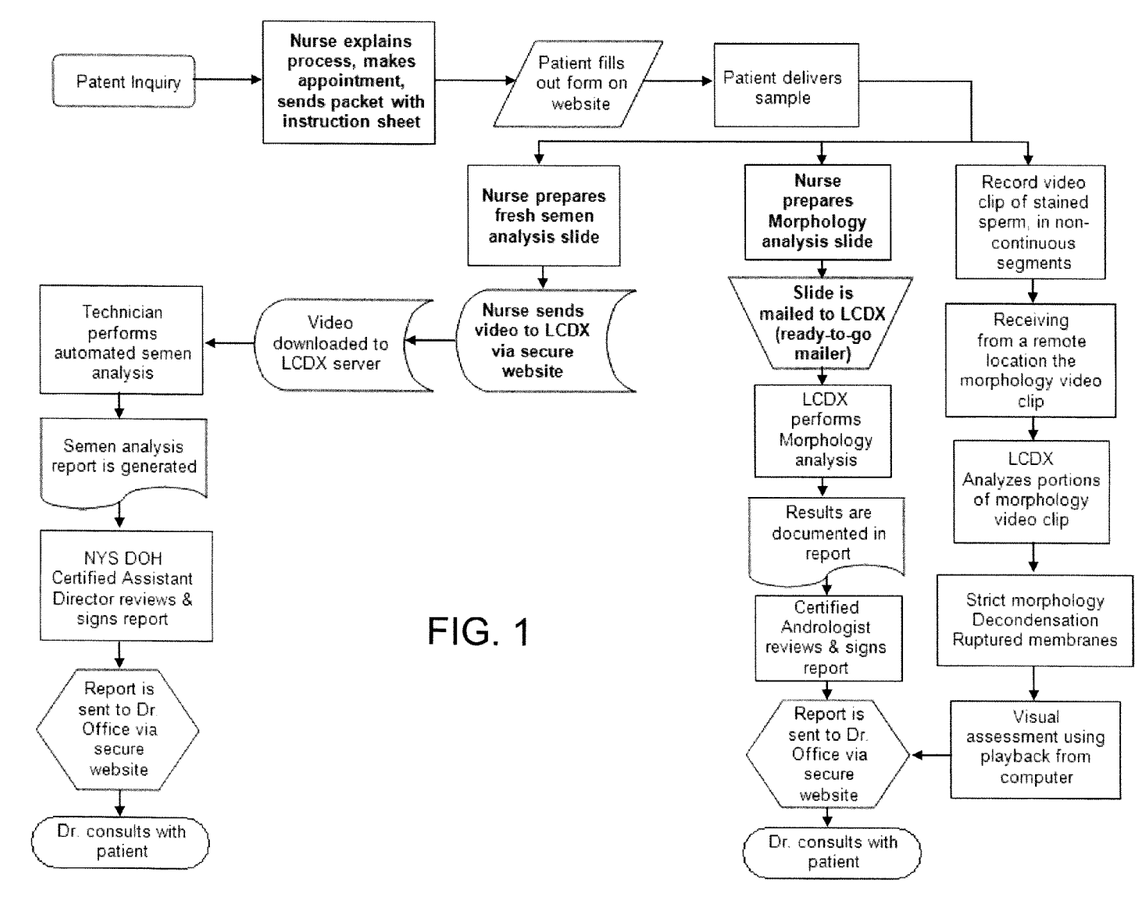
FIG. 1 is a flow chart depicting an embodiment of a method of processing a semen sample for remote analysis.

The present invention includes a method of collecting and preparing a semen sample for remote advanced semen analysis. The remote site, for example, an affiliate laboratory or affiliate site, will have technicians, nurses or other individuals trained in a number of specimen handling and testing procedures. As set forth in FIG. 1, the affiliate site will set a patient appointment, provide the patient with a set of instructions, as well as specimen container(s) and a transport (holding) medium.

Figure 2:
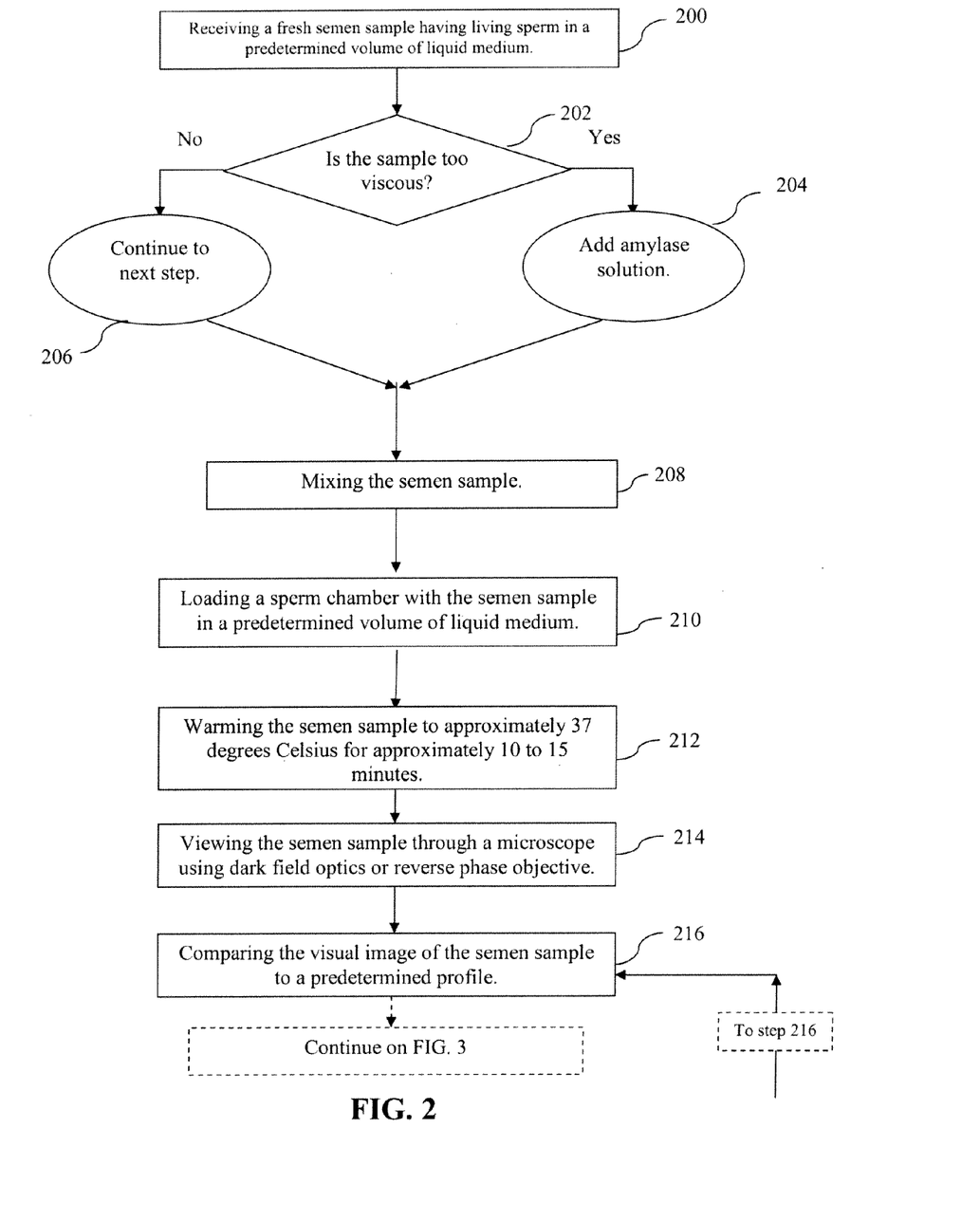
FIG. 2 is a flow chart depicting an embodiment of a method of preparing a semen sample for remote analysis.

As shown in FIG. 2, a fresh semen sample is received from the patient after the appointed period of abstinence. The semen sample may be collected in a single container, or in a split container, having a first and second chamber. The first chamber is arranged to collect a first portion of ejaculate, which typically has a higher sperm concentration, and the second chamber is arranged to collect a second portion of ejaculate, which typically has a lower sperm concentration. The collected semen sample is identified with the patient's information, which may include the patient's initials and a company's identification number(s). Then, basic tests are performed on the semen sample. For example, the pH is measured and recorded and the viscosity is analyzed as set forth in step 202. For example, the sample's uniformity, stringiness, thickness are determined. Many semen samples are highly viscous and cannot be properly handled. They are too viscous (like gel) or stringy and cannot be easily loaded into a sperm chamber (flat tube, Cell-Vu, etc.). The loading problem leads to errors in sperm count, and in estimating the percentage of sperm moving. To eliminate the viscosity problem, approximately 100 to 300 microliters of Amylase solution can be added to a portion of the semen sample, for example, 0.5 mL of the semen sample, and mixed according to step 204 and 208. The portion of semen sample is allowed to sit at room temperature or 37 degrees Celsius for approximately 5 to 30 minutes. If the portion of semen sample is still too viscous, an additional 100 to 300 microliters of Amylase solution can be added to the 0.5 mL of the sperm sample. Again, the 0.5 mL semen sample is mixed and allowed to sit for approximately 5 to 30 minutes. When the semen sample with Amylase solution is liquid enough to handle, the trained individual can proceed to preparing the semen sample for recording a motility digital video clip and a morphology digital video clip.

It should be appreciated that before the patient arrives, or during the sample handing, the following equipment will be turned on: microscope, specimen warming apparatus, computer, such as a laptop, and digital camera. The camera cord is connected to the laptop, and the camera program is opened. The semen sample motility digital video clips will be viewed with the 10× or 20× objective. The semen sample morphology digital video clips, as discussed below, will be created with the 100× objective. Depending on patient history, the semen sample will be loaded into one of several sperm chambers provided. For example, a Cell-Vu for high sperm counts, or a 100-micron deep glass flat tube for moderate counts can be used. If the sample was received as a split ejaculate in a split container, both the semen sample in the first chamber and the second chamber will be analyzed. The sperm warming device is mounted on the microscope stage and the loaded sperm chamber is laid on the glass unit. The controller is viewed to determine whether the "Ready" light is ON, and the 37 degrees Celsius signal is lit. Then one focuses the microscope on the moving sperm and views the moving sperm by watching their images on a monitor, including but not limited to a laptop monitor. The dark field is then adjusted as set forth in Step 214.

Using the living semen sample, the overall number of moving sperm, and their relative density in the sperm chamber, is quickly assessed and the quality of the image is quickly reviewed. For example, a trained individual determines if the sperm concentration is too high or too low for creating an acceptable video file. One also determines if many of the sperm out are out of focus, if the lighting is too bright to follow the sperm heads, etc. The trained individual will refer to the original training scenarios, protocols, ready-to-use training videos and the Model Video examples, as resources. These various tools serve as the predetermined profile against which the trained individual will make comparisons as set forth in step 216. With each new semen sample, the individual is trained to compare the current image on the computer monitor against the many profile images and profile standards, according to steps 216 to 224.

The trained individual will correct any focus problems, make adjustments in brightness or lighting, correct any problems with the dark field, etc., based on factors, including but not limited to, past training, experience with the training tools, and reference to the predetermined profile standards.

If the concentration of the motile sperm in the semen sample, is too low, the trained individual will reload a sperm drop or aliquot in an alternative sperm chamber. If concentration is too high relative to the predetermined profile standards, the trained individual will follow the sequential 1:2 dilution protocol as set forth in step 222. The trained individual will arrive at a sperm concentration and camera, light, microscope combination that is acceptable based on the predetermined profile. Once the semen sample is acceptable according to the predetermined profile, and once the sample has warmed to 37 degrees Celsius for 10 to 15 minutes, the trained individual will proceed to capturing a set of motility digital video clips as set forth in step 226.

The trained individual at the remote site should thoroughly complete the a checklist, which records dilution, sperm handling, holding medium, camera program settings, length of video recording, etc. In addition, the trained individual may complete the patient questionnaire form. The checklist may include a visual assessment of percentage motile wherein the percentage of sperm moving in the fresh, live sample is recorded. The set of data recorded on the check list will accompany the digital video clips, which may be transmitted to the central laboratory. In an embodiment of the invention, the digital video clips are transmitted to the central laboratory over the internet.

An exemplary camera that can be used is an Image Source camera capable of providing a high frame rate option of 60 frames per second. The selected camera must meet the imaging demands of the sperm since sperm heads are very small, approximately 7 microns, and since sperm move rapidly, up to 300 microns/second, and rotate while swimming and appearing as flashes of light. Also, the camera must have software corresponding to the needs of Computer Assisted Semen Analysis instruments.

For the selected camera, settings include image sequence, exposure, gamma, sharpness, white balance, color, and zoom. In addition, the MPEG4 codec and BY8 option for video size, and other settings, may be required. The start video record sequence requires that the trained individual notates the total number of frames taken. For example, for the motility videos, 5 seconds of video could represent 300 frames. Depending on the sperm chamber selected and the concentration of motile sperm, the patient folder may need four motility digital video files or even ten or more motility video files. Once the patient folder is complete, the folder is uploaded to a secure archival site, such as, Sharefile. The remote site and the trained technician have a password and a unique, secure folder, where all of the patient folders for the remote site reside. Each remote site can only open their patient folders.

Next, a morphology digital video clip is created. It should be appreciated that the word Morphology indicates simply the shape of the sperm cells: perfectly normal, borderline, double tails, very large heads, etc. The Morphology portion of an advanced semen analysis can also include assessment of the cap on the sperm head, called acrosome, and other features. The morphology analysis first involves novel steps in the staining of the sperm slide. The methods also use digital video files for carrying out remote morphology analysis. Two unique assays that stem from the special staining will be discussed at the very end: 1) sperm chromatin decondensation, and 2) sperm ruptured membranes.

Whether the sperm are received fresh in the central laboratory or a video is received remotely, a morphology smear is created. A drop is placed on a slide and smeared across, then dried. The slide is stained with the Diff-Quick kit, but with modifications. More specifically, methanol is used as the fixative and a water rinse is used in between each staining step. We have discovered that these modifications enhance weaknesses inherent in the sperm of men who are infertile.

A problem with creating digital video files of an aliquot of a semen sample on a slide for analysis is that there can be background debris, areas with too few sperm, and areas with too many sperm. This method for analyzing the slide by means of capturing a 10 to 20 second digital video clip can help alleviate these problems. That is, instead of creating 30 digital still photos or images of a semen sample at a remote site, and sending it through the internet, one to two video clips of 10 to 20 seconds in duration are captured.

To capture the digital video clip, a trained individual uses oil and the 100× objective on the microscope, to record a continuous 10 to 20 second digital video clip using the camera record mode. The trained individual will move the stained slide in a saw-toothed pattern during the recording, wherein there is no repeat recordation of the same area. For example, the trained individual will move the stained slide 1 mm, stop for a second or less, move 1 mm, stop for a second or less, etc. Thus, the camera keeps recording continuously, but the movement of the slide is not continuous. That creates perhaps 20 or 25 moments of no movement. If the count is low, additional morphology videos are made. For example, in an embodiment of the invention, four digital video clips can be captured.

The morphology videos are included in the patient folder that is uploaded to Sharefile and transmitted over the internet. During analysis at the central laboratory, a laboratory staff person will playback the video on a laptop or PC (using Windows Media Player, or similar). The staff person will hit the mouse at the "stop" moment to pause the video clip. During the pause, the staff person visually scans the sperm present in that one field of view. As the staff person visually scans the sperm, he or she will score each sperm as normal, abnormal, decondensed, ruptured, WBC, immature, etc. Then, the staff person hits the mouse and the video resumes to provide a new set of sperm in the field of view. The staff person will again pause the video to score the sperm in the field of view in the video. This process is repeated. If the male has very few sperm, the staff person may score every single sperm in the video clip, perhaps 75. If the male has many sperm, the staff person will score about 200 sperm, but will skip a majority of them. The result is transferred to the male's semen analysis report form.

Decondensation: The novel fixation and staining methods used led to a discovery that men who produce pregnancies have significantly fewer sperm with decondensation. This is observed as an abnormal spreading of the chromosomes that are packaged in the head (nucleus) of the sperm. Healthy sperm maintain "condensed" chromatin while weak sperm are not packaged correctly (histones, protamines) and have a greater tendency to "let go" and spread out.

The statistical cut-off value used is 14%. If a morphology slide shows 14% of the sperm heads with decondensation, then this semen sample is NOT behaving like sperm from fertile men. The morphology video files also show decondensation clearly. Settings for color, size and contrast make this possible.

Ruptured Membranes: The novel fixation and staining steps described above have also revealed another difference between men who produce pregnancies, and those who do not produce pregnancies. The slides, and digital video clips, show a higher number of sperm with broken cell membranes (ruptured membranes). This appears as dark or red dots around the circumference of the sperm head. Remote video files can also be accurately scored for this phenomenon. Again, correct camera and lighting settings are needed including color, brightness, size, etc. Our statistical cut-off value is 7%. Most fertile men have <7% of the sperm with ruptured membranes.

Figure 3:
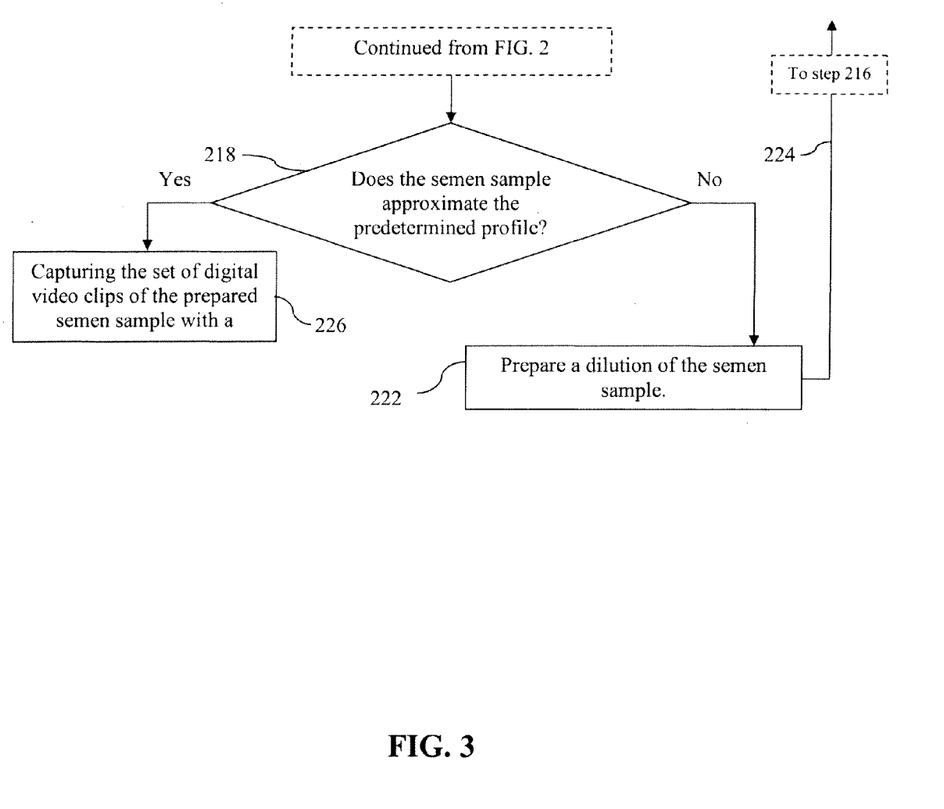
FIG. 3 is a flow chart depicting an embodiment of a method of preparing a semen sample for remote analysis.

Referring to FIGS. 2 and 3, an embodiment of a method of preparing and analyzing a semen sample having living sperm is shown. Generally, a semen sample is received, according to step 200, in a split container, or a single container, which holds a predetermined volume of liquid medium. In an embodiment of the invention, the predetermined volume of liquid medium is approximately 3 ml. In a preferred embodiment, the holding medium is a culture medium, such as Ham's F10 medium. According to step 202, if the semen sample is too viscous, approximately 0.1 ml amylase solution is added to the semen sample in the liquid medium, as shown in step 204 and as described in more detail above. If the semen sample is not too viscous, one may proceed to the next step according to step 206 without adding amylase solution. According to step 208, the semen sample is mixed and the sample is then loaded into one of several sperm chambers, according to step 210. The semen sample is warmed at approximately 37 degrees Celsius, according to step 212 for approximately ten to fifteen minutes. As indicated in step 214, when the semen sample image is transmitted through the microscope and camera onto the laptop screen, then the visual image of the semen sample is compared to a predetermined profile according to step 216. In an embodiment of the invention, the semen sample is viewed using dark field optics or a reverse phase objective. An exemplary microscope that can be used to view the semen sample is the trinocular Model manufactured by Labomed. It should be appreciated by those having ordinary skill in the art that the microscope was modified to permit dark field imaging. The predetermined profile is illustrated using visuals aids, such as digital training video clips or digital images, representing the preferred appearance of the semen sample before a video image is captured, as well as clear examples of a negative condition, that is, conditions that are not desirable. For example, the predetermined profile may include certain visual aids illustrating the approximate number of motile sperm at the recommended magnification. In an embodiment of the invention, the predetermined profile may also include the preferred brightness and/or darkness of the semen sample when viewed on the monitor of a computer, the preferred focus, the preferred concentration, etc. According to step 218, it is determined whether the semen sample approximates the predetermined profile. If it is determined that the semen sample does approximate the predetermined profile, a set of motility digital video clips of the prepared semen sample is captured using a video capture device, such as a camera coupled to the microscope, according to step 220. An exemplary camera used to capture the digital video clips is a CCD camera having a model number AS manufactured by Image Source. The set of motility digital video clips is acquired at a location that is remote from the central laboratory where the digital video clips of the semen sample are further analyzed. In an embodiment of the invention, the digital video clips are transmitted over the internet from the remote site to the central laboratory. It should be appreciated by those having ordinary skill in the art that by remote it is meant two geographically separated facilities, each facility can be located in any part of the world.

If it is determined that the semen sample does not approximate the predetermined profile because the approximate number of sperm per field is too high, a dilution of the semen sample is prepared as indicated in step 222 and as described in further detail above. According to step 224, step 216 of comparing the semen sample to a predetermined profile, through step 222, are repeated until it is determined that the semen sample approximates the predetermined profile. It should be appreciated by those having ordinary skill in the art that the dilutions of the semen sample are preferably a series of 1:2 dilutions of semen sample to culture medium until the approximate number of sperm observed on the monitor of the laptop provided approximates the profile. For illustrative purposes, a semen sample as received may be diluted 1:2. If it is determined that the semen sample is too concentrated, the semen sample is diluted 1:2 again providing an actual dilution of 1:4.

Figure 4:
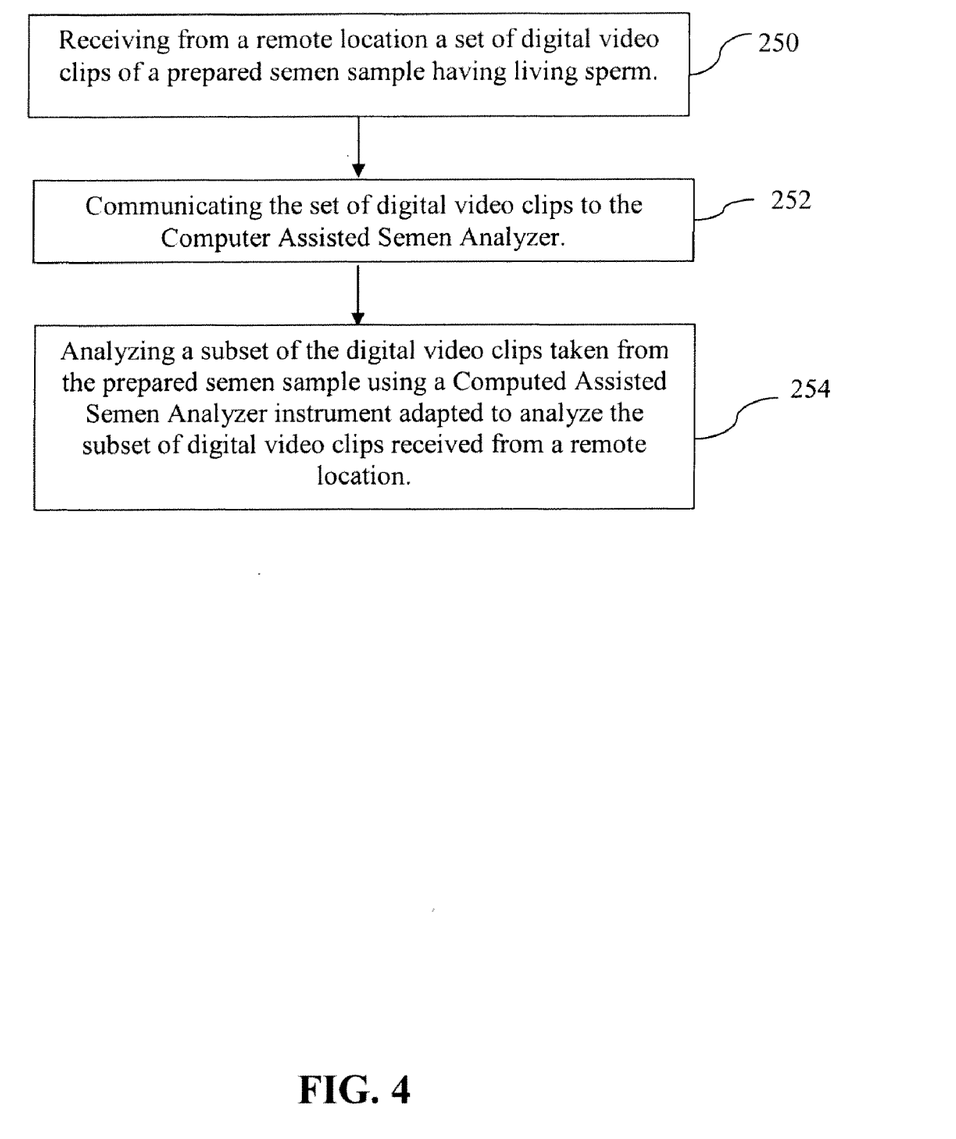
FIG. 4 is flow chart depicting an embodiment of a method of analyzing a semen sample received from a remote location.

As shown in FIG. 4, according to step 250, a set of digital video clips of a prepared semen sample having living sperm is received from a remote location. As indicated by step 252, the set of digital video clips are communicated to a Computer Assisted Semen Analyzer (CASA). A subset of digital video clips taken from the prepared semen sample is analyzed, according to step 254. That is, approximately four to forty digital video clips are recorded and transmitted to the central laboratory wherein each video has a duration of approximately 0.5 seconds to five seconds. In an embodiment of the invention, each video has a duration of five seconds. A portion of the digital video clips, for example 0.5 seconds to 3.5 seconds of the digital video clips, are analyzed. In an embodiment of the invention, portions of a subset of the set of digital video clips are analyzed. For example, one second portions of a subset of ten out of fifteen digital video clips may be analyzed to determine sperm motility. Analyzing digital video clips that are at least one second in duration is preferred to capture the intermittent swimming at high velocities of sperm.

Figure 5:
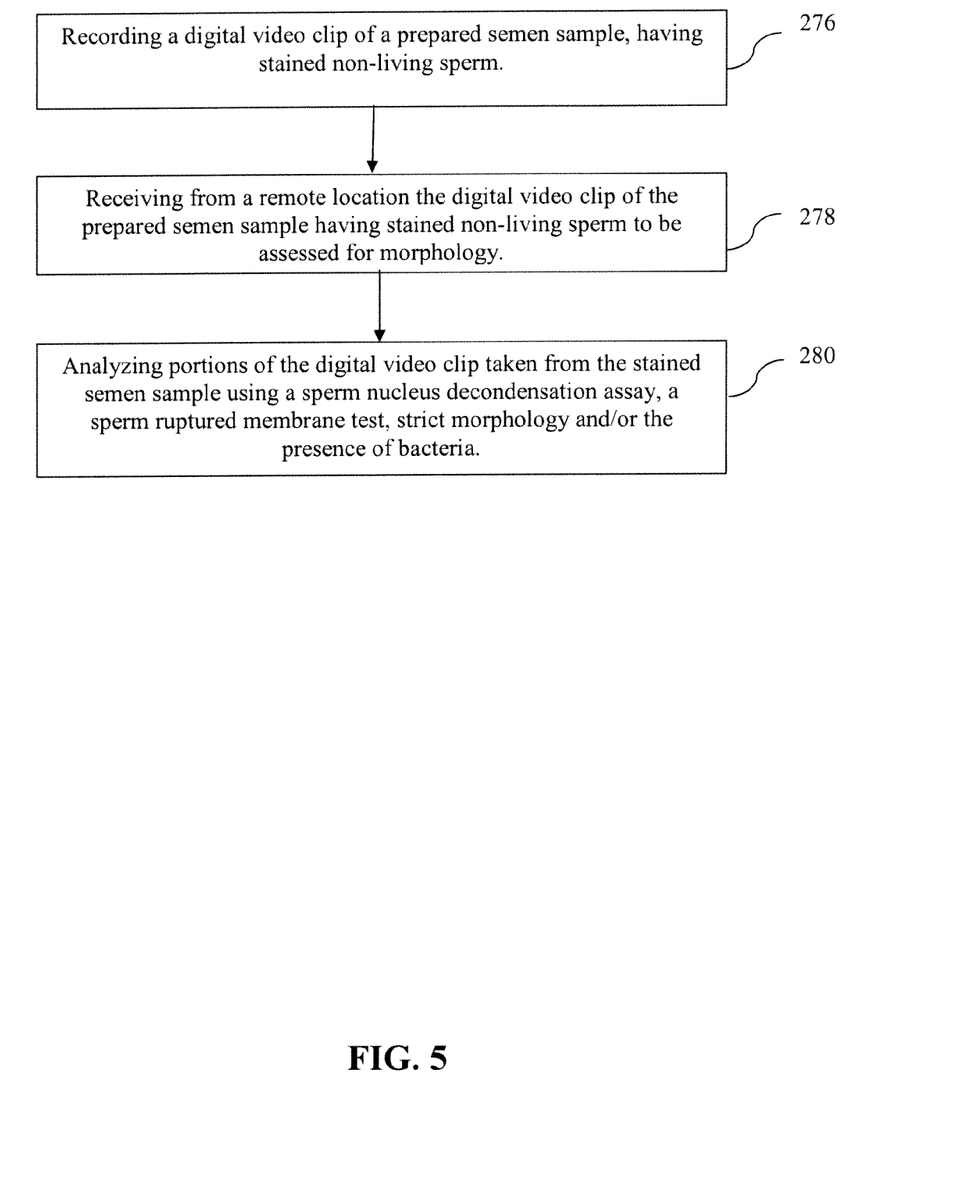
FIG. 5 is a flow chart depicting an embodiment of a method of analyzing sperm morphology of a semen sample received from a remote location.
Figure 6:
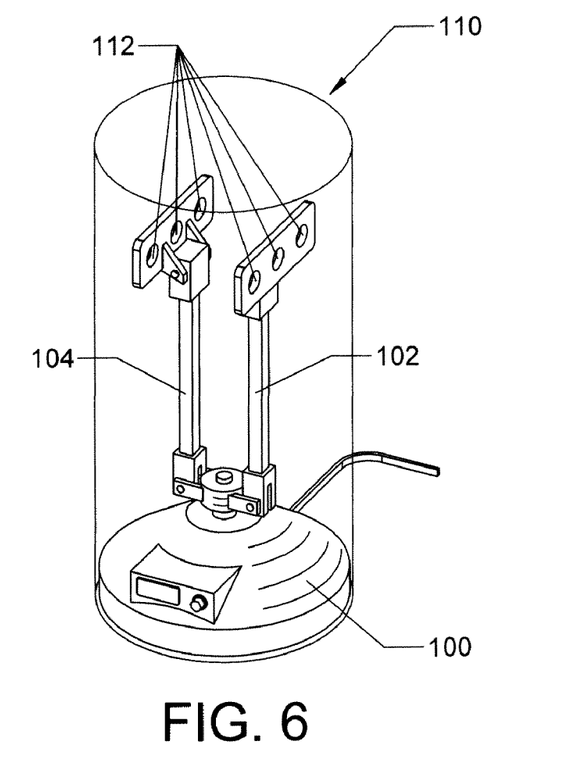
FIG. 6 is a perspective view of a centrifuge having arms capable of moving approximately ninety degrees.
Figure 7:
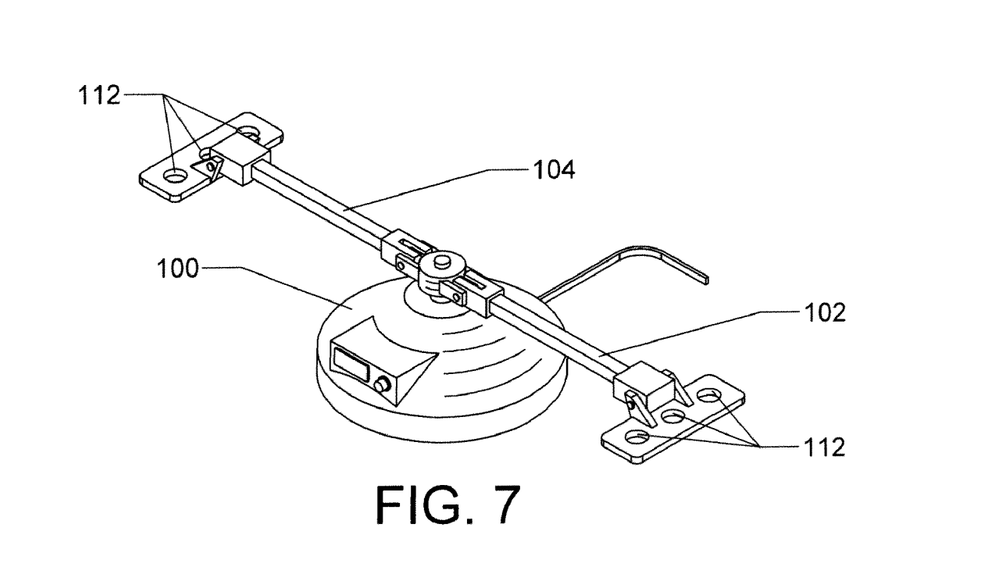
FIG. 7 is a perspective view of the centrifuge shown in FIG. 7 with the arms in an open position and with the cover removed.
Figure 8:
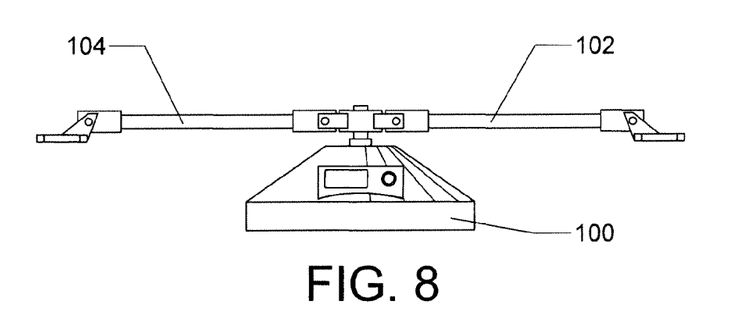
FIG. 8 is a side view of the centrifuge shown without the cover.
Figure 9:
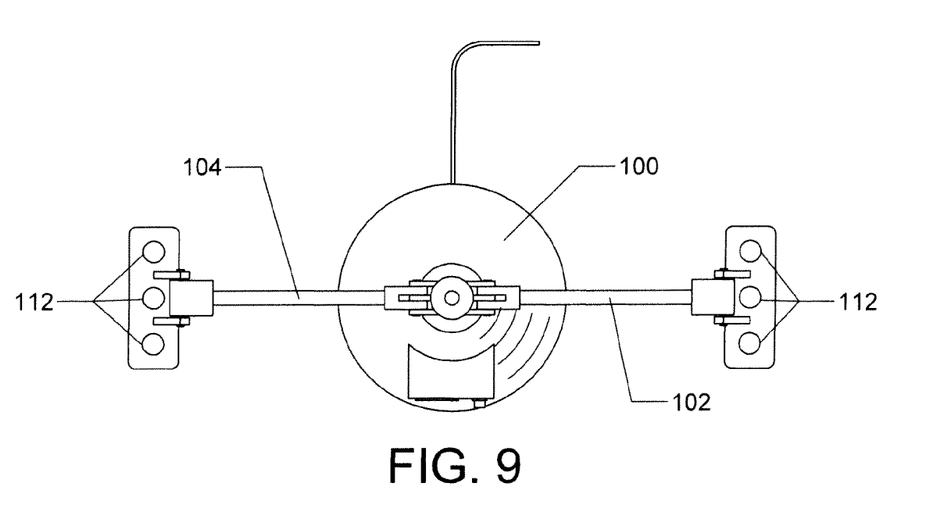
FIG. 9 is a top view of the centrifuge shown without the cover.
Figure 10:
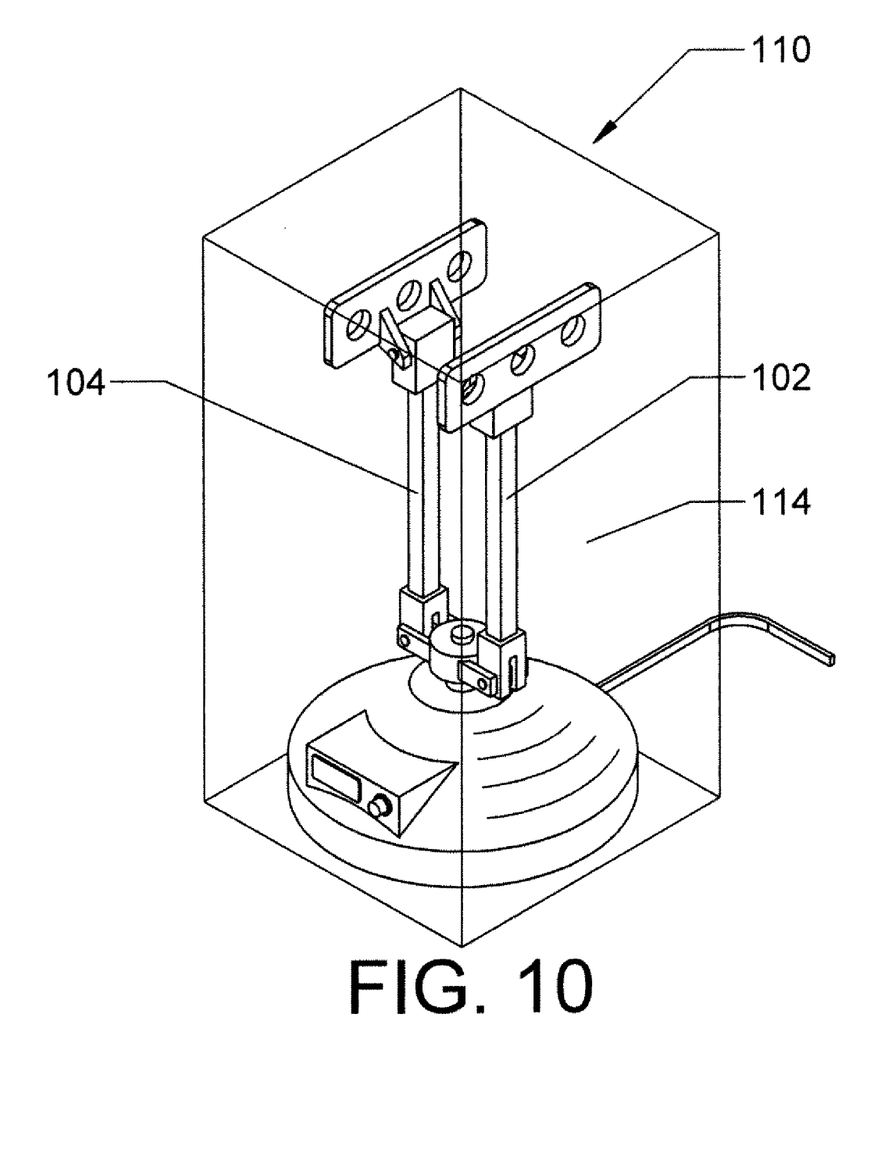
FIG. 10 is a perspective view of the centrifuge shown with the cover.
Figure 11:
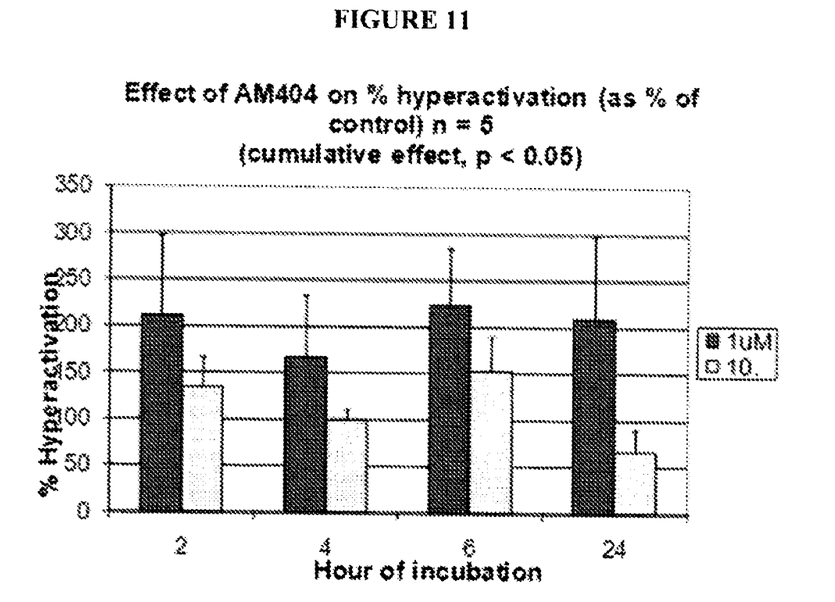
FIG. 11 is a graph illustrating the effect of AM04 on percentage hyperactivation.
Figure 12:
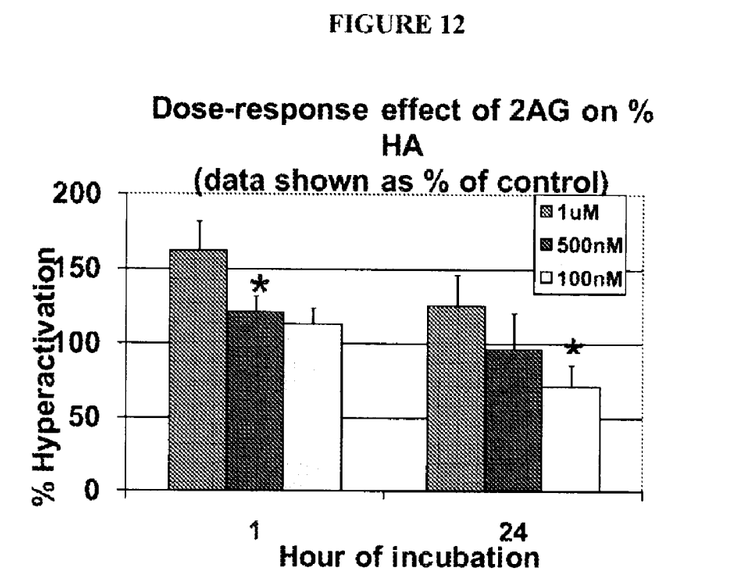
FIG. 12 is a graph illustrating the dose-response effect of 2AG on percentage HA.

As shown in FIG. 5, according to step 276, a digital video clip of a prepared semen sample having stained non-living sperm is recorded at a remote location as described above. Then, the digital video clip of approximately 10 to 20 seconds in duration is received from the remote location to be assessed for morphology according to step 278. At the central laboratory, portions of the digital video clip are analyzed. For example, as described above, the following tests can be conducted using the digital video clip to assess the morphology of the sperm: sperm nucleus decondensation assay, sperm ruptured membrane test, strict morphology, including sperm shape, number of immature sperm cells, number of white blood cells, and/or the presence of bacteria.

Referring to FIGS. 6-10, a centrifuge having a base 100 and two arms 102, 104 moveable between a first resting position and a second operational position is shown. Infertility clinics tend to have very small lab spaces. They have difficulty finding enough counter space for the equipment package, and many of them do not have a centrifuge. Centrifuges are used to spin the tube of diluted semen, used for washing the sperm, and also used for creating a better morphology slide. The present invention centrifuge is small and inexpensive, filling the need for the remote affiliate sites.

More specifically, the base 100 can be cast iron, providing the weight and stability required, although it should be appreciated that other types of bases may be possible. The base 100 is approximately 8 to 12 inches in diameter. The base 100 is equipped with a suction cup mechanism (not shown), in order to secure the centrifuge 110 securely to a mounting surface such as a counter top. The two swinging arms 102, 104 are 10 to 12 inches in length (radius) and are centrally attached. Each arm includes three apertures 112 to support 3 sleeves permitting the centrifuge 110 to hold a maximum of 6 disposable centrifuge tubes (15-mL in volume). However, it should be appreciated by those having ordinary skill in the art that a greater or fewer number of apertures with corresponding sleeves (not shown) can be included. The arms 102, 104 are "swing-out", meaning that their orientation moves to horizontal as centrifugal force increases. The small motor is housed in the base 100. Sperm are very fragile and must be centrifuged/washed at low "g" forces. Therefore, the motor is designed to produce a maximum force of 300 g (factors of radius, rpm; not variable, all or nothing). When not in use, the swinging arms 102, 104 can be folded vertically to an approximately 90 degree position from the open and moving position, and are held in place with a clear plastic cover 114. It should be appreciated by those having ordinary skill that other types of covers may be used. This frees up counter space for other operations in the remote site.

Fertilization in humans and animals requires normal ovulation of the egg, transport of the egg into the Ampulla of the oviduct (mammals), and arrival of a few sperm that are fully Capacitated. Capacitation involves a number of changes in seminal sperm that prepare the sperm to locate the egg, approach the egg cover (zona), bind to the zona, penetrate the zona and contact the living egg cell.

Fertility is closely tied to the ability of the ovulated egg to bind to the sperm, initiate fertilization events, cleave into 2 cells and grow from there. Contraception research has been most successful when focused on events in the female, particularly altered ovulation, ability of the egg to bind to sperm, blocking of development in the fertilized egg, transport of the growing embryo to the uterus, and implantation.

The class of chemicals called Cannabinoids includes the natural chemicals found in our bodies (endocannabinoids, ECB) as well as cannabinoids found in the marijuana plant. Nicotine is also found in a plant (tobacco leaf) and has a natural counterpart in our bodies (acetylcholine, cholinergic receptors). Both acetylcholine and the ECB chemicals—anandamide and 2-arachidonoylglycerol—play an important role in regulating many functions, in many tissues of humans and mammals.

Numerous cannabinoid ligands—those chemicals that bind to the cannabinoid receptors (CBR)—can alter fertilization, alter events in mammalian eggs, and have good potential as contraceptive agents.

Many categories of CB receptor (CBR) ligands exist. These include reuptake inhibitors for the natural anandamide (ANA), enzyme inhibitor, transport inhibitor, receptor agonists, and receptor antagonists. Some of the ligands are natural, and many are synthetic.

According to the examples below, cannabinoid receptor ligands can be used as contraceptive agents—as inhibitors of ovarian, egg, and embryo events. Secondly, cannabinoid receptor ligands can be used as contraceptive agents, which alter testis or sperm functions which are required for fertilization.

Individual studies show: (i) the natural anandamide is found in moderately high levels in human oviductal fluid, human follicular fluid, and human semen; (ii) UCM blocks vigorous swimming of human sperm, hence adecreased potential for binding to the human egg; and (iii) OMDM decreases the potential of human sperm to bind to the egg, and penetrate the egg, thus decreased fertilization capacity.

Brief Guide to Cannabinoid System Compounds

| COMPOUND | BINDING CHARACTERISTIC | DESCRIPTION |
| --- | --- | --- |
| Anandamide | Endogenous CB1 agonist = | AEA (arachidonoyl-ethanolamide) |
| Meth-anandamide | CB1 agonist = | R-methanandamide Synthetic |
| 2-AG | Endogenous CB1 agonist = | 2-arachidonoyl-glycerol |
| AM-1346** | CB1 agonist | Synthetic |
| AM-411 | CB1 agonist | Synthetic |
| AM-251 | CB1 antagonist | Synthetic, nearly identical to Rimonabant |
| 2-AG ether | CB1 agonist | |
| OMDM | Inhib anandamide reuptake | Synthetic |
| UCM 707 | ECB transport, FAAH inhibitor | synthetic |
| AM-630 | CB2 antagonist | Synthetic |
| AM-404 | Reuptake inhibitor | Synthetic |
| AM-1241** | CB2 agonist | Synthetic |

**Not commercially available

Studies show the cannabinoid implications in vivo in the mouse model. In separate experiments, mouse sperm are pre-treated with Meth-anandamide or AM-1346 and then the mouse sperm are inseminated into the mouse uterus (artificial insemination).

TABLE 1

Effect of Cannabinoid Receptor Agonists on mouse fertilization and embryo development:

| | Control | 100 nM | Signif. |
| --- | --- | --- | --- |
| Methanandamide | | | |
| Number embryos per female | 7.7 ± 0.7 | 4.3 ± 0.7 | p < 0.01 |
| % ova as 1-cell on Day 1 | 67.4% | 91.3% | p = 0.03 |
| Number of 2-cells on Day 1 | 2.5 ± 0.4 | 0.6 ± 0.2 | p < 0.05 |
| % embryos >2-cell on Day 3 | 60.5% | 25.0% | p < 0.01 |
| % embryos degenerated on Day 3 | 6.5% | 44.2% | p < 0.001 |
| AM-1346 | | | |
| % 1-Cell Day 1 | 29% | 65% | p < 0.001 |
| % Fertilized (cleaved) Day 1 | 41% | 19% | p < 0.001 |
| % Morula Day 2 | 22% | 9% | p < 0.003 |
| % Degenerated Day 3 | 58% | 70% | p = 0.05 |

Each egg could be scored as 1-cell, 2-cell, 3-4 cell, 5-8 cell, morula, blastocysts or degenerated. Brief exposure of the sperm to the drug before insemination produces significant inhibition of 5 parameters. Compared to Control, the treated animals ovulate fewer ova (p<0.01, t-test). Compared to the Control, the treated animals have a higher percentage of ova as 1-cell on Day 1 (p=0.03, chi-squared), that is, fewer eggs are fertilized or, if fertilized, they do not cleave. By Day 2, treatment produces a lower % of 2-cell eggs—again, fewer eggs are cleaving. By Day 3, treatment shows a significantly lower % of eggs that have developed beyond the 2-cell—embryo development is severely retarded. On Day 3, treatment shows a much higher % of degenerated eggs compared to the Control. The drug severely impairs fertilization and embryo development.

Methanandamide shows a biphasic effect: Higher concentrations produce inhibition and could lead to reduced fertilization capacity.

Anandamide in higher concentrations trends towards reduced fertilization capacity.

Alpha fetoprotein (AFP) is a fetal protein that is dominant during early embryonic development, in mammals and humans. AFP can originate from both fetal and cancer tissues, and causes growth enhancement in its native form. However, segments of AFP can produce growth suppression and has received much attention in the cancer arena.

There is interest in a 34-amino acid portion of AFP (34-AA peptide segment), and other AFP synthetic analogs that are growth inhibitory. Human sperm contain the receptors for a large number of regulatory substances found in the body (cannabinoid, cholinergic, opiates, estrogen, dopamine, etc.). Sperm show changes in fertilization functions when incubated with several AFP related peptides.

Data collected indicate that one or more peptides can have contraceptive action and that Synthetic AFP-derived peptides, as a class of compounds, can be used as contraceptive agents in mammals. Further, small AFP-derived peptides, 8 to 200 amino acids in length, effect reproductive functions: blocking ovarian function, ovulation, fertilization of eggs, development of embryos, implantation, testicular function, spermatogenesis, sperm capacitation, sperm binding to eggs, sperm fertilization of eggs.

Fertilization assays include changes in human sperm vigorous swimming (Hyperactivation, computer-tracking), changes in % moving, and changes in the ability of drug-treated sperm to complete the acrosome reaction, and ability to bind to the human egg cover (Hemizona assay).

In Summary, these several peptides produced statistically significant inhibition of human sperm % motility (30% decline), binding to the human egg cover (55% drop; 40% drop); vigorous swimming patterns (40% loss; 30% loss; 50% loss).

Those skilled in the art will recognize that modifications may be made in the method and apparatus described herein without departing from the true spirit and scope of the invention which accordingly are intended to be limited solely by the appended claims.

The invention claimed is:

1. A method of analyzing a semen sample comprising:
    warming a prepared semen sample to approximately 37° C.;
    capturing, with a camera coupled to a microscope at a location remote from a Computer Assisted Semen Analyzer, a set of digital video clips of the prepared semen sample having living sperm at a frame rate of at least 50 images per second and of approximately 0.5 seconds to 5 seconds in duration;
    receiving, by a hardware component, from the remote location the set of digital video clips of the prepared semen sample over a network; and
    analyzing portions of each digital video clip in a subset of the set of digital video clips by said Computer Assisted Semen Analyzer.

2. The method of analyzing a semen sample of claim 1, wherein the set of digital video clips of the prepared semen sample are transmitted over an internet.

3. The method of analyzing a semen sample of claim 1, wherein the step of capturing the set of digital video clips further comprises recording approximately 4 to 40 digital video clips.

4. The method of analyzing a semen sample of claim 3, wherein the step of analyzing a subset of the set of digital video clips further comprises analyzing between approximately 0.5 seconds to 3.5 seconds of selected digital video clips.

5. The method of analyzing a semen sample of claim 3, wherein between approximately 100 and 10,000 frames are captured in each set of digital video clips.

6. The method of analyzing of a semen sample of claim 1, wherein the step of capturing the set of digital video clips further comprises recording approximately 5 digital video clips.

7. The method of analyzing semen sample of claim 1, wherein the step of analyzing a subset of the set of digital video clips further comprises analyzing at least 1.0 second of selected digital video clips.

8. The method of analyzing a semen sample of claim 1, wherein the semen sample is from a human.

9. The method of analyzing a semen sample of claim 1, wherein the semen sample is collected from an animal.

* * * * *